(12) United States Patent
Lindahl et al.

(10) Patent No.: US 9,737,336 B2
(45) Date of Patent: Aug. 22, 2017

(54) ANATOMICALLY PERSONALIZED AND MOBILIZING EXTERNAL SUPPORT AND METHOD FOR CONTROLLING A PATH OF AN EXTERNAL AUXILIARY FRAME

(71) Applicant: Aalto University Foundation, Aalto (FI)

(72) Inventors: Jan Erik Lindahl, TKK (FI); Jari Salo, Kerava (FI); Jukka Tuomi, TKK (FI); Roy Björkstrand, TKK (FI); Mika Salmi, TKK (FI); Eero Huotilainen, TKK (FI); Mikko Roiha, TKK (FI)

(73) Assignee: Aalto University Foundation, Aalto (FI)

( * ) Notice: Subject to any disclaimer, the term of this patent is extended or adjusted under 35 U.S.C. 154(b) by 0 days.

(21) Appl. No.: 14/580,247

(22) Filed: Dec. 23, 2014

(65) Prior Publication Data
US 2015/0112339 A1    Apr. 23, 2015

Related U.S. Application Data

(63) Continuation-in-part of application No. 14/285,726, filed on May 23, 2014, which is a continuation of (Continued)

(30) Foreign Application Priority Data
Oct. 5, 2009    (FI) ..................................... 20096019

(51) Int. Cl.
*A61B 17/70* (2006.01)
*A61B 17/62* (2006.01)
(Continued)

(52) U.S. Cl.
CPC .............. *A61B 17/62* (2013.01); *A61B 5/103* (2013.01); *A61B 5/1116* (2013.01);
(Continued)

(58) Field of Classification Search
CPC ......... A61B 17/60; A61B 17/62; A61B 17/64; A61B 17/6416; A61B 17/6425;
(Continued)

(56) References Cited

U.S. PATENT DOCUMENTS 4,637,382 A    1/1987 Walker
5,122,140 A    6/1992 Asche et al.
(Continued)

FOREIGN PATENT DOCUMENTS

EP    0248138 A1    12/1987
JP    S62286455 A    12/1987
(Continued)

OTHER PUBLICATIONS

Bottlang, M. et al.: "Articulated external fixation of the ankle: minimizing motion resistance by accurate axis alignment", Journal of Biomechanics, 32, 1999, p. 63-70.
(Continued)

*Primary Examiner* — Lynnsy Summitt
(74) *Attorney, Agent, or Firm* — Seppo Laine Oy

(57) ABSTRACT

The invention concerns an anatomically personalized and mobilizing external support configured to be arranged to support a physical joint between a first and a second bone group, which support comprises at least one first external auxiliary frame, which is configured to be attached to the first bone group using invasive attachment means, at least one second external auxiliary frame, which is configured to be attached to the second bone group using invasive attachment means, and at least one external auxiliary joint, which is fitted between the first and the second auxiliary frame. The
(Continued)

external support is configured to permit a rotation of the second external auxiliary frame relative to the first external auxiliary frame about a rotational axis, sliding of the rotational axis relative to the first external auxiliary frame in a first direction, and sliding of the rotational axis or at least a portion of the second external auxiliary frame relative to the first external auxiliary frame in a second direction, which differs from the first direction.

9 Claims, 5 Drawing Sheets

Related U.S. Application Data application No. 13/499,911, filed as application No. PCT/FI2010/050756 on Sep. 30, 2010, now Pat. No. 8,777,946.

(51) Int. Cl.
A61B 17/64 (2006.01)
A61B 5/103 (2006.01)
A61B 5/11 (2006.01)
A61B 5/00 (2006.01)

(52) U.S. Cl.
CPC .......... *A61B 5/1121* (2013.01); *A61B 5/1124* (2013.01); *A61B 5/4528* (2013.01); *A61B 5/4595* (2013.01); *A61B 17/6425* (2013.01); *A61B 5/6878* (2013.01)

(58) Field of Classification Search
CPC .............. A61B 17/6441; A61B 17/645; A61B 17/6458; A61B 17/6466; A61B 17/6475; A61B 17/6483; A61B 17/6491; A61B 17/66; A61B 17/663; A61B 19/50; A61B 17/025; A61B 2017/0268; A61B 2019/508
See application file for complete search history.

(56) References Cited

U.S. PATENT DOCUMENTS

| 5,928,234 | A | 7/1999 | Manspeizer |
| 5,941,877 | A | 8/1999 | Viegas et al. |
| 6,205,411 | B1 | 3/2001 | DiGioia et al. |
| 6,355,037 | B1 | 3/2002 | Crosslin et al. |
| 7,383,164 | B2 | 6/2008 | Aram et al. |
| 7,881,771 | B2 | 2/2011 | Koo et al. |
| 2003/0191466 | A1 | 10/2003 | Austin et al. |
| 2004/0073211 | A1 | 4/2004 | Austin et al. |
| 2005/0020909 | A1 | 1/2005 | Moctezuma de la Barrera et al. |
| 2005/0215997 | A1 | 9/2005 | Austin et al. |
| 2005/0267722 | A1 | 12/2005 | Marquart et al. |
| 2007/0161984 | A1* | 7/2007 | Cresina .............. A61B 17/6425 606/54 |
| 2008/0051685 | A1 | 2/2008 | Benenati et al. |
| 2009/0299368 | A1 | 12/2009 | Bauer |

FOREIGN PATENT DOCUMENTS

| JP | 2006519636 A | 8/2006 |
| JP | 2007020881 A | 2/2007 |
| WO | WO9619944 A1 | 7/1996 |
| WO | WO 9710775 A2 | 3/1997 |
| WO | WO 2004070573 A2 | 8/2004 |
| WO | WO2004071309 A1 | 8/2004 |
| WO | WO 2009106816 A1 | 9/2009 |

OTHER PUBLICATIONS

MacWilliams, B., "A comparison of four functional methods to determine centers and axes of rotations". Gait & Posture, Nov. 2008, vol. 28, No. 4, pp. 673-679, doi: 10.1016/j.gaitpost.200805.010 section "2. Methods" on pp. 674-675.

O'Hara B.P. et al.: "Influence of cyclic loading on the nutrition of articular cartilage", Annals of the Rheumatic Diseases, 49, 1990, p. 536-539.

Ristiniemi, Jukka et al.:"Two-ring Hybrid External Fixation of Distal Tibial Fractures: A Review of 47 Cases", The Journal of Trauma Injury, Infection and Critical Care, Jan. 2007, vol. 62, No. 1, p. 174-183.

Watson, J. Tracy et al.: "Pilon Fractures, Treatment Protocol Based on Severity of Soft Tissue Injury", Clinical Orthopaedics and Related Research, vol. 375, 2000, p. 78-90.

Yoon H.K. et al., "Computer and Robotic Model of External Fixation System for Fracture Treatment", Computational Science—ICCS 2004.

* cited by examiner

ANATOMICALLY PERSONALIZED AND MOBILIZING EXTERNAL SUPPORT AND METHOD FOR CONTROLLING A PATH OF AN EXTERNAL AUXILIARY FRAME

RELATED APPLICATIONS

This application is a Continuation-in-Part of U.S. patent application Ser. No. 14/285,726, filed on May 23, 2014, which is a Continuation of U.S. patent application Ser. No. 13/499,911, filed on Sep. 3, 2010. The subject matter of which are incorporated by reference herein in their entirety.

FIELD OF THE INVENTION

Aspects of the present invention relate to tissue-damage rehabilitation devices and methods. In particular, aspects of the invention relate to an anatomically personalized and mobilizing external support and to the creation of external support for damaged tissue, in order to support the tissue during rehabilitation. Other aspects of the present invention relate to methods for controlling a path of an external auxiliary frame.

BACKGROUND ART

As is known, the care of serious damage to a synovial joint resulting from accidents is challenging. For example, falling accidents often result in serious damage to the ankle, which is caused by the ankle bone impacting the cartilage surface of the tibia, which in the worst case can even lead to the crushing of the lower end of the tibia. Recovery from injuries like those described usually takes several months. In typical care following a falling accident, the damaged ankle is repaired operatively and fixed, i.e. supported rigidly, using, for example, so-called pilon rings and similar care accessories. However, in order to recover to full functionality, the cartilage requires nutrition, the transportation of which—unlike that in other tissues—is based on the tissue being loaded in cycles, so that fluid dynamics appear inside the cartilage. The recovery of cartilage is described in detail in the publication, 'Influence of cyclic loading on the nutrition of articular cartilage' (O'Hara B., Urban J., & Maroudas A., Ann. Rheum. Dis. 1990 July; 49(7): 536-539). If mobilization that transports nutrients is not arranged, the cartilage surface repaired by the operation may be destroyed, which will be followed in a couple of years by a state corresponding to osteoarthritis, i.e. invalidity. Precisely because osteoarthritis patients are mostly young people or those of working age, such as building workers, invalidizing osteoarthritis leads to not only personal misfortune, but also a significant economic cost.

In the publication 'Articulated external fixation of the ankle: minimizing motion resistance by accurate axis alignment' (Bottas M., March. L., & Brown T., Journal of Micromechanics, Vol. 32, No. 1, January 1999, pp. 63-70), it is stated that factors promoting recovery from, for example, the ankle-fracture injuries referred to above are protection from loads, early post-operative movement, a reduction in splinter fractures, and minimal disturbance of the injured area. For this reason, post-operative supports for damaged joints have been developed, so that in aftercare it will be possible to take into account mobilization of the joint as a precondition for recovery. However, it should be noted that, besides the mobilization of a damaged joint, its correct timing is of considerable significance in the success of rehabilitation. For example, the mobilization of an ankle must be started already two days after an operation. Correspondingly, a movement of the wrong kind can have disadvantageous consequences. It is therefore of decisive importance to find the joint's anatomically correct path, in order to minimize the resistance to motion and avoid sudden damage caused by the wrong kind of movement. Thus, significant expectations are directed to post-operative supports, in relation to both being able to be rapidly installed and to creating the correct type of path.

Many external supports are known. However, the majority of supports intended for the aftercare of synovial joint injuries are either rigid, i.e. the supports do not permit therapeutic movement, or supports permitting movement, the motion permitted by which is typically a rough approximation of the real movement of the joint. In a hinge joint, such the ankle, movement takes place around only a single axis of rotation, with a limited extent of movement. This is the simplest model of a moving joint, due to which it is used as an illustrative example in this connection. In other types of synovial joint, rotation and sliding in the direction of several axes or planes of movement can take place simultaneously. These can be controlled equally by means of the technology disclosed here. Rigid supports are, among others, Ilizahrov rings, which are external supports attached on both sides of the damaged joint. Ilizahrov rings are a way of implementing joint support that penetrates the tissue, i.e. it is invasive. In the method, the rings are attached to the patient's bone by using tensioning cables and bone screws. Ilizahrov rings and their use are described in greater detail in the publications 'Pilon fractures. Treatment protocol based on severity of soft tissue injury' (Watson J. T., Moed B. R., Karges D. E., Cramer K. E. Clin. Orthop. 2000; 375: 78-90) and 'Two-ring hybrid external fixation of distal tibial fractures: A review of 47 cases' (Ristiniemi J., Flinkkilä T., Hyvönen P., Lakovaara M., Pakarinen H., Biancari F., Jalovaara P., J. Trauma 2007; 62: 174-183), the contents of which is included in this as a reference. In addition, non-invasive rigid supports are known, such as traditional plaster casts and similar. Supports permitting movement have been created, for example, by arranged external hinge-type plates, with the aid of which an attempt has been made to imitate the movement of the damaged joint. An example of the said plate in cases like the ankle fracture described above is a kind of pedal, on top of which the base of the foot is placed and which is adjusted to permit only such a tilting movement as would be natural for a healthy ankle.

Alternative methods are known for defining the natural movement of a synovial joint. In camera-based methods, the movement is recorded by using, for example, a video camera and alignment marks, which are attached to the object to be moved. After recording the movement, the preferably digital video material is analysed using special software and the movement information obtained with the aid of the alignment marks is captured, in order to form the path of movement. This method is utilized widely, for example, in sports applications and in the film industry, for which the technology was originally developed. Because the method does not require physical contact with the patient, the method is quite user-friendly from the patient's point of view. The accuracy of the method varies from the accuracy required for making animations to the accuracy required for quality control. However, in the final resort the accuracy of the method depends on the resolution of the camera and on the measurement volume used. Typically, sufficiently accurate information is obtained by means of the method for animation of the movement of an entire limb, but this technology does not provide an answer to the movements of the bones that act as counter-surfaces in an individual joint. A drawback of the method is that, in terms of the area of the theme of the invention, the method cannot be used to determine reliably the movement of the bones under the actual tissues, but rather the movement of the tissue on top of the bones. In addition, these methods do not reveal the fine-dynamic flexing under the soft tissue, i.e. the dynamics between the bones. Because it has not been possible to accurately define the precise anatomic movement, it has also not been possible, on the basis of these methods, to design anatomically personalized external supports.

An alternative to camera-based methods are three-dimensional or radiographic methods, in which a three-dimensional model of the bones is formed on the basis of either computer tomography (CT) or magnetic-resonance imaging (MRI). The methods are suitable for modelling the shape of an individual bone. MRI is not, however, suitable for situations in which non-MRI compliant screws are used, for example certain steel screws or other attachment means, in the area of the joint already attached for old injuries or installed for the care of a new injury. In the said cases, CT imaging would be a possible method, but it suffers from imaging interference caused by metals and from the great radiation stress caused to the patient.

In known applications, a damaged synovial joint and its part are modelled on the basis of CT or MRI, when a virtual kinetic model corresponding to the damaged joint is obtained. This solution has been typically used in early motion analysis studies of cases of injury, because the technology used has been readily available in a hospital environment. For example, publication US2008312659 discloses a method for manufacturing a prosthesis, in which a patient-specific image, which is used as an aid in the manufacture of the prosthesis, is formed from data obtained from MRI imaging. For its part, publication US2007118243 discloses a method, in which a computer-based model, which is exploited to manufacture implants, prostheses, and similar, is created from data obtained on the patient's anatomy in CT imaging. Though CT and MRI-based methods are indeed suitable for the manufacture of patient-specific artificial joints and other implants, the use of the said methods does not achieve sufficient accuracy as would permit preserving and saving a patient's own joint after injury. Traditionally, it has been possible to achieve an accuracy of about 10 millimeters, whereas achieving a good result would require an accuracy of at least 1 . . . 3 millimeters, preferably at least 0.5 millimeters. Typically, significant swelling also occurs in the area of a limb joint after injury, which reduces the accuracy if the definition of movement or the support is based on skin contact.

In general, significantly unknown tolerances relate to the technology used in the creation of bone models, which derive from the imaging quality and the grey-tome values available in sectioning. In addition, the joints, locations, and attitudes of three-dimensional models are fitted together visually in a 3D environment, which further reduces the method's reliability and repeatability. Tolerance errors made in the creation of bone models accumulate, when the attachment points are designed on the basis of the models. All in all, at least up until now, the CT and MRI-based three-dimensional method have not been applied, because sufficient accuracy cannot be achieved using the methods.

Thus, the problems of the prior art are related to the determining of the path of a damaged joint. Because each joint, tissue, and injury is different, a statistical approximation and present modelling methods have not been able to provide a solution for creating an anatomically personalized support. More specifically, using present post-operative external supports, i.e. supports external to the body, it has not been possible to place artificial or auxiliary joints sufficiently precisely on the paths of movement of the joint, so that the mobilization of an injured limb or similar will not succeed, due to which the cartilage of the joint will not receive nutrition reliably. As stated, in mechanical design, as is known, reference geometries can be utilized, either by creating them in a three-dimensional 3D-CAD system, or by bringing a camera-based digital geometry to the design system, by using various methods and various formats. Challenges generally arise in the combination of a reliable design geometry, referencing digitalization, and a real application. Thus, the known joint supports have been rigid, which is not optimal from the point of view of the recovery of a joint.

The external support devices on the market, which a priori permit movement to a limited extent around a single axis, are in point of departure universal-type devices. It has therefore not been possible to take into account the size of the patient or soft-tissue damage, which are important in terms of avoiding complications. In these cases, the attachment spikes must be placed in an area that has been very precisely defined beforehand, while the location of the external axis cannot be determined other than visually with the aid of transillumination. The precision then remains unavoidably poor and the path small.

It is an object of the present invention to solve at least some of the drawbacks of the prior art and to create an improved method for creating a anatomically personalized and mobilizing external support for rehabilitating a synovial joint.

SUMMARY

The object of certain embodiments of the invention is to provide an anatomically personalized and mobilizing external support configured to be arranged to support a physical joint between a first and a second bone group.

A current one-axis external fixator apparatus having both bone screws and the rotation axis organized in one plane cannot provide a large range of motion. Therefore, a problem in clinical work is that one-axis fixator joints do not provide enough mobility and the post-treatment range of the motion is decreased.

It is in particular an object of certain embodiments of the invention to provide an anatomically personalized and mobilizing external support between a first and a second bone group which improves mobility.

Another object of certain embodiments of the present invention is to provide a method for controlling a path of an external auxiliary frame of an anatomically personalized and mobilizing external support.

These and other objects are achieved by the embodiments of the present invention, as hereinafter described and claimed. According to an aspect, embodiments of the invention concern a new type of external support to be fitted between the bone groups, which comprises at least one first external auxiliary frame, which is configured to be attached by invasive attachment means to the first bone group, at least one second external auxiliary frame, which is configured to be attached by invasive attachment means to the second bone group, at least one external auxiliary joint, which is arranged between the first and second auxiliary frame, as well as at least one personalized adapter component, which is arranged to connect the auxiliary joint to the auxiliary frame. The external support is configured to permit rotation of the second external auxiliary frame relative to the first external auxiliary frame about a rotational axis or centre point, sliding of the rotational axis or centre point relative to the first external auxiliary frame in a first sliding direction, and sliding of the rotational axis or at least a portion of the second external auxiliary frame relative to the first external auxiliary frame in a second sliding direction, which differs from the first sliding direction. In other words, the second external auxiliary frame is rotatably connected about an axis of rotation via the auxiliary joint to the first external auxiliary frame. Further, it is possible to offset the axis of rotation in a first direction and in a second direction. By means of the rotation about one axis of rotation and two translations in two different directions, any desired movement of the second external auxiliary frame in a two-dimensional plane relative to the first external auxiliary frame can be achieved. The external auxiliary joint is made by an additive manufacturing, machining or casting such to be non-adjustable.

In an embodiment, the at least one external support is further configured to permit an alteration of the radius of the rotational axis relative to a stationary swing axis.

According to an embodiment, the external support is configured such that the radius of a path of the rotational axis relative to a stationary swing axis is in the range between 10 [mm] and 60 [mm].

According to another embodiment, at least one personalized adapter component, which is arranged to connect the auxiliary joint to the first auxiliary frame.

In an embodiment, the first sliding direction is arranged perpendicular to the second sliding direction.

In another embodiment, in the auxiliary frames there are measurement points, which are arranged to receive the measuring head of a coordinate measuring device. According to other embodiments, it is possible to use, for example, a three-dimensional laser scanner or a camera based device for measurement.

According to an embodiment, the at least one external auxiliary joint is adjustable in such a way that the angle between the at least one external auxiliary joint and the movement of a patient's joint between the first and second bone group can be adjusted.

According to another embodiment, the external support comprises bone screws or cables or both as invasive attachment means for fixing the at least one first external auxiliary frame and the at least one second external auxiliary frame to the first and second bone group, respectively.

According to another aspect of the invention, there is provided a method for controlling a path of a second external auxiliary frame of an anatomically personalized and mobilizing external support relative to a first external auxiliary frame, the method comprising:
  rotating the second external auxiliary frame relative to the first external auxiliary frame about a rotational axis,
  offsetting the rotational axis relative to the first external auxiliary frame in a first direction, and/or
  offsetting the rotational axis or at least a portion of the second external auxiliary frame relative to the first external auxiliary frame in a second direction, which differs from the first direction.

According to an embodiment, the radius of the rotational axis relative to a stationary swing axis is adjusted.

In an embodiment, a path of movement of a bone group relative to another bone group is measured with the aid of a part of the external support invasively attached to at least one of the said bone groups before rotating the external auxiliary frame, offsetting the rotational axis in the first direction, and offsetting the rotational axis or at least a portion of the external auxiliary frame in the second direction.

In another embodiment, the radius of the path is in the range between 10 [mm] and 60 [mm].

According to an embodiment, the first direction and the second direction are perpendicular to the rotational axis. According to another embodiment, the first direction is also perpendicular to the second direction.

Considerable advantages are achieved with the aid of the embodiments of the invention. A new type of an external support to be fitted between the bone groups is provided. Based on latest ankle movement modeling it is found that the rotation axis of the ankle complex is not stationary but moves. The embodiments of the invention provide three degrees of freedom of the second external auxiliary frame relative to the first external auxiliary frame in a two-dimensional plane, thus improving position adjustment of the second external auxiliary frame relative to the first external auxiliary frame in order to improve mobility. The radius of the path $r(t)$ of the rotational axis relative to a stationary swing axis can be personalized by means of an offsetting rotational axis. According to certain embodiments, it is for example possible to vary the radius of the path $r(t)$ in the range between $r(t)=10$ [mm] and $r(t)=60$ [mm]. As a result, the path of the rotational axis of the second external auxiliary frame does not describe a circle, but continuously or step-wise changes its radius $r(t)$ relative to the stationary swing axis, thus describing, for example, an elliptical path.

By means of a certain embodiment of the invention, a particularly accurate model of the movement of the damaged joint can be achieved by measurement, thanks to which it is possible to design, manufacture, and install a precisely anatomically personalized and mobilizing external support.

Because a precise anatomical correspondence with the patient's own joint is obtained from the mobilizing external support, the movements to be performed in post-operative rehabilitation will imitate the natural path of movement of the joint. In particular, the offsetting rotational axis of the external auxiliary joint improves imitation of the natural path of movement of the second external auxiliary frame. Thus, thanks to this movement, the joint will receive nutrition promoting recovery and the wrong kind of movement will not cause additional damage to the joint. In terms of the success of later rehabilitation, both the preservation of muscle control and the prevention of contraction (shrinkage) of the tendons are very important. Complete locking of a joint for even a few weeks will lead to detectable movement restrictions and also to immobilization osteoporosis. However, with the aid of the embodiments of the invention these problems can be reduced.

The accurate patient-specific path of movement of the joint also permits the use of soft fillers as a basis for the regeneration of the structural parts of the joint. Thus, for the duration of recovery, the path of movement of an extensively damaged joint is controlled using the external support device according to certain embodiments of the invention, in such a way that the movement takes place the whole time in a controlled manner, without a deforming force being directed to the soft medium before it has regenerated sufficiently to form a load-bearing cartilage and bone under the cartilage. At the same time, the embodiments of the invention permit controlled movement exercises of the joint, for example, as aftercare of ligament repairs.

Because, in the method according to certain embodiments of the invention, it is possible to use devices, which have been demonstrated to be reliable in other connections, the performance of each sub-area of the method has been optimized separately. This is because according to one embodiment the supports to be attached to the bone group are Ilizahroz rings, which are a particularly advantageous way of attaching external structures to limbs. Correspondingly, according to one embodiment the measurement of the path of movement is performed using a coordinate measuring device, which has been shown in an engineering-shop environment to be suitable for even demanding quality-control and even calibration applications. Thus, the method can be implemented using very different device combinations, the parts of which have been proved to be good in other connections. Thus, the method is not dependent on new technologies untried in practice.

According to one embodiment, the external support's auxiliary joint is adjustable, so that the movement permitted for a joint that has been operated on can be adjusted as recovery progresses. For example, the bone groups surrounding an injured joint can be locked to be immobile for a couple of days after the operation, after which by adjusting the external support's auxiliary joint rehabilitation can be commenced in stages according to the conditions for recovery, in the cases of both the extent of movement and the degrees of freedom of the selected movements. At a later stage during recovery, the external support can be completely unlocked in order to provide maximum mobility by means of rotation of the second auxiliary frame about one axis of rotation and two translations of the rotational axis in two different directions, thus enabling the second auxiliary frame to move along a path having a varying radius $r(t)$ relative to a stationary swing axis though the radius of each point of the second auxiliary frame is constant. Depending on measurements previously done, the varying radius $r(t)$ can be personalized in order to improve mobility. The motion of the external support according to certain embodiments of the invention is more natural than the motion of a support having a constant radius r relative to a stationary swing axis.

In addition, certain embodiments of the invention permit the attachment spikes to be placed entirely freely, so that, for example, the damaged areas of the soft tissues can be left free, thus reducing the risk of complications. This also provides a possibility of choice to exploit the points achieving the best skeleton grip in the bone attachments and both to accelerate the operation as well as to reduce the amount of x-rays used in the operating theatre.

BRIEF DESCRIPTION OF THE DRAWINGS

For a more complete understanding of particular embodiments of the present invention and their advantages, reference is now made to the following descriptions, taken in conjunction with the accompanying drawings. In the drawings.

DETAILED DESCRIPTION OF EMBODIMENTS

The method according to certain embodiments of the present invention can be applied to the care of numerous different joint injuries. The method according to the embodiments of the invention is particularly suitable for, but not restricted to, the care of traumatic changes. Because joint injuries are caused to a very great extent as a result of falling accidents, the method according to the invention will be described hereinafter in the case of an example of an ankle fracture, because it is an anatomically simple subject. Of course, the method according to the invention is also suitable for creating the external supports required in the case of other joint injuries. A typical pilon fracture is associated with a falling accident that has taken place due to negligence in work safety, or in connection with a physical hobby, as a result of which the patient's ankle bone has impacted the cartilage surface of the tibia, which has resulted in damage to the joint between the ankle bone and the tibia. In the worst case, the entire under surface of the tibia will have shattered.

Figure 1:
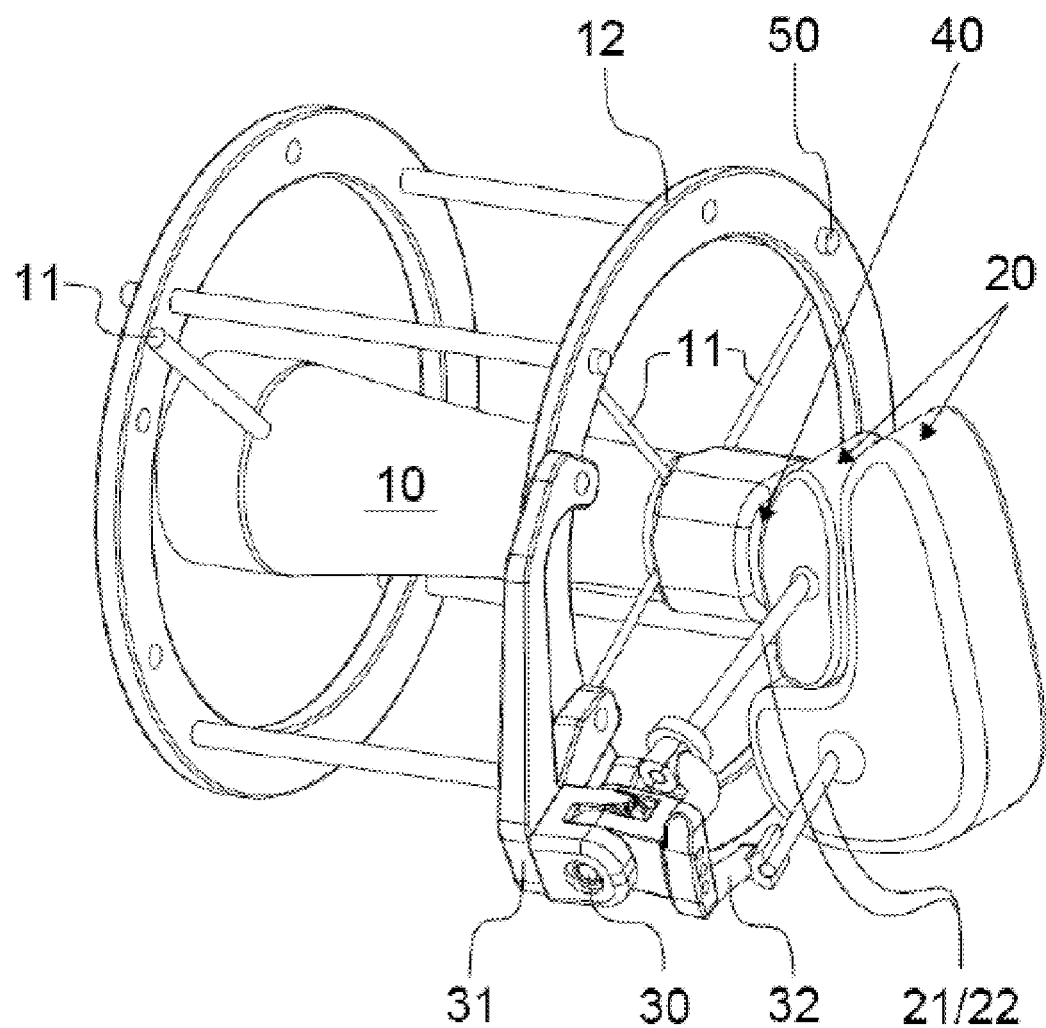
FIG. 1 presents a person's ankle, to which an external support has been fitted.

In FIG. 1 an example of an anatomically personalized and mobilizing external support is illustrated. The damaged joint 40 is surrounded by at least two bone groups: a first bone group 10 and a second bone group 20. In the case of the example of the anatomically personalized and mobilizing external support between a first and a second bone group described here, the first bone group 10 is the tibia and the second bone group 20 is the ankle bone and the heel bone connected to it. In this connection, a group of bones, which consists of at least one bone, is regarded as being a bone group. In the case of the ankle-fracture example, the first bone group 10 thus comprises only a single bone and the second bone group 20 comprises two bones. Immediately after the injury has occurred, the patient's ankle is typically fixed, i.e. supported rigidly using splints, a plaster cast, an external attachment device (external fixator), or some other rapidly applicable means, by which movement of the ankle is prevented. Often, swelling caused by the injury prevents the fracture pieces from being immediately returned to their places and the related internal attachment using screws, spikes, plates, or other implants. If the soft-tissue situation permits, the ankle is operated on, in connection with which the pieces of cartilage are lifted off the tibia and returned to their original location. Traditionally, in the operation fixation is performed using an Ilizahrov or other rigid support device, which is known.

According to the ankle example, in connection with the operation, auxiliary frames 12, 22 are placed around the damaged joint 40, with the aid of which an anatomically personalized and mobilizing external support can be designed, manufactured, and installed outside the joint 40, which will permit the joint 40 to be able to be moved to the correct extent in the correct directions, according to all the directions of movement required and measured in each joint. The auxiliary frames 12, 22 are attached invasively to the bone groups 10, 20 surrounding the joint 40, for example, using bone screws or various suitable cable arrangements. In this connection, the term invasive refers to a part penetrating tissue and the term external refers to a part outside the tissue. In the example of FIG. 1, two invasive bone screws 21, which form the second attachment means, are attached to the second bone group 20. The first auxiliary frame 12, which is attached to the first bone group 10 invasively with the aid of the first attachment means, which comprise the bone screws and cables according to FIG. 1, is fitted to the first bone group 10 surrounding the joint 40. The first auxiliary frame 12 may be, for example, an Ilizahrov ring arrangement, which is easy to fit to the tibia according to the ankle example.

In the attachment of the auxiliary frame, the actual attachment point is, according to certain embodiments of the invention, of no particular importance: the attachment point, for example for bone screws, is chosen on the conditions of the best possible contact and the most accommodating soft-tissue situation. Also the position and attitude of the auxiliary frame 12, 22 can be selected quite freely, but, however, in such a way that the distance of the closest point of the auxiliary frame from the coming external auxiliary joint is the smallest possible, either by visual estimate or by calculation.

As can further be seen from FIG. 1, the second auxiliary frame 22 fitted to the second bone group 20 comprises the heads of the bone screws 21. Alternatively, the second auxiliary frame 22 could be, for example, a horseshoe-shaped ring resembling an Ilizharov ring, which is attached to the second bone group by bone screws 21. Generally, the auxiliary frame according to certain embodiments of the invention can be an arbitrary component, which can be fixed to the bone group and to which an auxiliary joint 30 or adapter 32, which will be dealt with in greater detail later, can be fitted externally.

Once the injured joint 40 has been repaired in an operation and the external auxiliary frames 12, 22 has been fitted to the bone groups 10, 20 surrounding the joint 40, the movement of the joint 40 is modelled for the design of a correct type of mobilizing external support. Immediately after the operation, the joint 40 is, however, fixed temporarily, for example for a couple of days, by securing the auxiliary frames 12, 22 to each other by a suitable intermediate part. According to certain embodiments of the invention, prior to this the movement is modelled using a digitalization device, by means of which numerical and correct information is created. In this connection, the term digitalization refers to a device, by means of which movement information can be captured from a physical object and data, such as a set of coordinates, for processing is created. According to one embodiment, the digitalization device is a coordinate device, for example the MicroScribe MX, by means of which in the best case accuracy of as much as 0.05 millimeters can be obtained. Alternatively, it is possible to use, for example, a three-dimensional laser scanner, the use of which has, however, usability problems, because the application of the measurement information created using the scanner in an external set of coordinates is challenging. When using a coordinate measurement device, the measuring device and the subject of the measurement must be placed mutually in the same set of coordinates. In practice, the coordinate measurement device and the first auxiliary frame 12 are supported, in the ankle example presented, in an operating theatre on furniture in such a way that the distance or attitude between them does not move during the measurement. In order to facilitate the measurement, seatings 50, in which there is a recess 51 for the measuring head of the coordinate measurement device (FIGS. 1 and 2), are fitted to the auxiliary frames 12, 22. Thanks to the recess 51, the measuring head of the coordinate measurement device cannot slide away from the measuring point, in order to improve the reliability and repeatability of the measurement.

Figure 2:
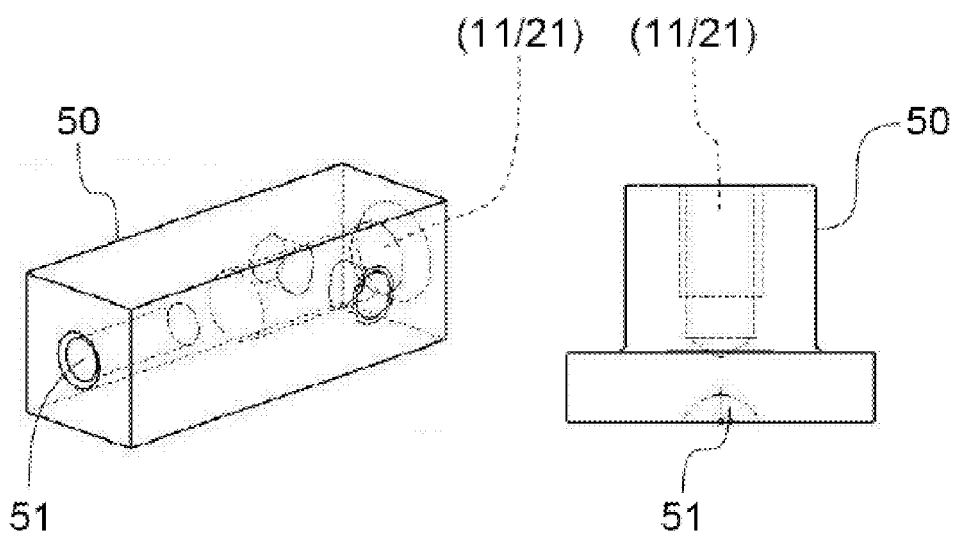
FIG. 2 presents a seating used in measurements.

As FIG. 2 shows, the seating 50 is, according to one example a stud, which is attached to a hole in the auxiliary frame 12, 22, and in which there is a recess 51 or cavity with the same diameter as the measuring head, into which the measuring head must be placed in the correct attitude. The left-hand side of FIG. 2 shows the seating 50, which is equipped with a long recess 51, so that the arm of the measuring head must be correctly aligned when the measuring head touches the bottom of the recess 51. The right-hand side of FIG. 2 show a seating 50 equipped with a shallow recess 51. In both seatings 50, there is a hole on the opposite side to the recess 51, which is arranged to receive the attachment element, by means of which the seating 50 is attached to the measurement object. The first auxiliary frame 12, 22 is designed in such a way that the measurement points of the seatings 50 placed in the holes are mutually on the same plane. Alternatively, a corresponding cavity or recess 51 for the measuring head of the measurement device, promoting the measurement, can be machined or otherwise precision-manufactured in the auxiliary frame 12, 22.

In the measuring process, the intention is to obtain information of the kinetic dynamics of the joint, i.e. as to how the bone groups around the joint move relative to each other, by means of the joint. More specifically, in the measurement, the movement between the first and second bone groups 10, 20 in respect to the joint 40 is measured with the aid of the auxiliary frames 12, 22 attached to the bone groups 10, 20 by attachment means 21. In the ankle example described above, the coordinates of the measurement points of the auxiliary frame 12 (Ilizahrov ring) attached to the first bone group 10, i.e. the tibia, are measured first. In the case of the example, at least three, preferably more, seatings 50 are attached to the first auxiliary frame 12. Because the first auxiliary frame 12 is designed in such a way that the recesses 51 in the seatings 50 are mutually on the same plane, it is easy, on the basis of the measurements to form a reference-geometry plane, which depicts the surface of the first auxiliary frame 12, to which the auxiliary joint 30 is attached. Thus, there must be at least three measurement points, in order to form each spatial plane. The measurement points are preferably more than three, because in that case measurement errors can be evened out by approximating the results computationally when forming the planes. In addition, it is good to repeat the number required, in order to eliminate measurement errors. In the case of the example above of an ankle joint, this is simplified to become a hinge joint.

Once the locations of the measurement points of the auxiliary frame 12 of the first bone group 10 have been measured, the path of the measurement point or points of the second auxiliary frame 22 relative to the first auxiliary frame 12 is measured. The path can be measured, for example, in such a way that the joint 40—in the case of the example of the ankle—is moved in a natural path relative to the joint 40, during which time at least three values are measured for the measurement point of the second auxiliary frame 22. Preferably as many attitudes as possible of the joint 40 on the path are measured repeatedly, in order to eliminate measurement errors and to determine the precise length of the path. The second auxiliary frame 22 is also preferably equipped with a seating 50 receiving the measuring head, especially preferably with a seating 50 according to the example on the left-hand side of FIG. 2.

Figure 3:
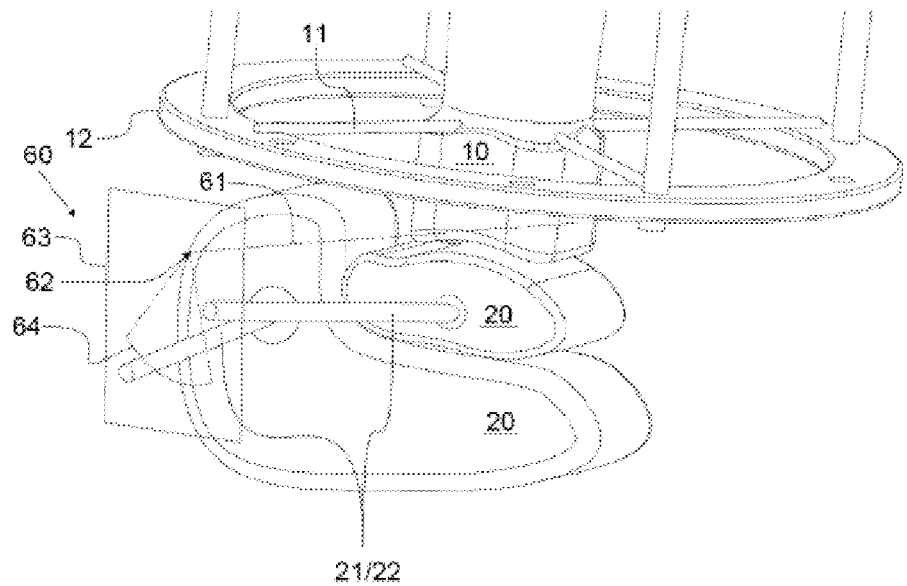
FIG. 3 presents a CAD view from the design of a support according to an example.

After, or during the measurements, the measurement data is transferred to a CAD system. According to one embodiment of the invention, the measurement data is transferred from the coordinate measuring device directly to the CAD system, either through a common interface, or with the aid of separate software. Alternatively, the information can also be recorded in a file, from which the measurements points are loaded as points into the CAD program. Once the measurement information is in the CAD system, the kinetic dynamics of the joint 40 are modelled on the basis of the information. In the modelling of the kinetic dynamics 60, the movement of the joint 40 can be approximated and modelled very accurately on the basis of the measurements obtained from the second auxiliary frame 22, by arranging the curve 64 to run through the measurement points (not imaginary), as shown in FIG. 3. On the basis of the curve 64, in the case of a hinge joint, the plane 63 of movement and the centre point 62, axis 61, and extreme points (ends of the curve) of the rotational motion can then be determined. In a joint comprising several degrees of freedom, each rotation and sliding movement combination is defined, as well as their mutual rhythm in each plane in a corresponding manner. On the basis of the measurement results obtained from the first auxiliary frame 12, it is possible, on the other hand, to create a reference plane, relative to which the second bone group 20, i.e. the second auxiliary frame 22, moves (not shown). The reference plane is created with the aid of at least three measured points, in which case the three points are set to connect the plane. The computational creation of paths of motion, planes, and axis on the basis of measured points is, as such, known.

According to certain embodiments of the invention, a CAD model is arranged from the auxiliary frames 12, 22. In this connection, the term arranging, refers to the fact that the CAD model is created either by procuring it in a ready-made form from a databank, in which the component has been modelled beforehand, or by forming a CAD model on the basis of an existing component. In terms of the performance of the invention, it is preferable for there to be a finished CAD model of the auxiliary frame, as well as of the components to be used, already prior to measuring, so that the operating time will not be taken up in modelling. According to one embodiment, the components used, such as the auxiliary frames 12, 22, the attachment means 21, and the auxiliary joint 30 are standard components, of which there are ready-made CAD models. The measurement points are also preferably modelled into the CAD models of the auxiliary frames 12, 22, so that the adaption of the models to the measured plane or measured axis will be easy. In addition, a CAD model is arranged of the auxiliary joint 30 (FIG. 1) used in the external support. The auxiliary joint 30 is preferably of a general-purpose model and a simple, readily available hinge-type pin joint, the path permitted by which can be limited mechanically. The hinge component can further be shaped according to modelling, in such a way that it permits sliding of the rotational centre point and the alteration of the radius of the path. This is necessary, for example, when modelling the movements of the knee.

Once the kinetic dynamics 60 of the joint 40 have been created in the CAD system, the arranged CAD models of the auxiliary frames 12, 22 are adapted to the path in the CAD system. In the case of the ankle example, the surface of the first auxiliary frame 12 closest to the second auxiliary frame 22 is placed, on the basis of the measurement results, in an attitude on the created plane (not shown), in which the measurement points coincide with each other. Correspondingly, the CAD model of the auxiliary joint 30 is placed on the path, in such a way that the axis of the auxiliary joint 30 and the axis 61 of the path coincide, so that the CAD model of the auxiliary joint 30 simulates the joint permitted by the path 64 brought into the CAD system. Preferably, kinetic centre point of the model of the auxiliary joint 30 coincides with the centre point 62 of the modelled motion. Once the length of the path is known on the basis of the model of the path, the extent of motion of the real auxiliary joint 30 is adjusted preferably to correspond to the measured natural extent of motion of the joint 40. Correspondingly, the CAD model of the second auxiliary frame 22 is aligned in place in the CAD system on the basis of the model of the path. The modelled measurement point or points are also preferably modelled in the CAD model of the second auxiliary frame 22.

Once the auxiliary frames 12, 22 and the auxiliary joint 30 have been adapted in the CAD system to the created path model, the necessary adapter components 31, 32 for connecting the auxiliary joint 30 to the auxiliary frames 12, 22 (FIG. 1) are modelled in the system. In some cases, the auxiliary joint 30 can be adapted to be connected directly to the auxiliary frame 12, 22, in which case only a single adapter component 31, 32 will be required. According to one embodiment, as shown in FIG. 1, an adapter component 31, 32 is designed between both the first and the second auxiliary frame 12, 22 and the joint 30. It is particularly advantageous to design the adapter components 31, 32 directly in the CAD system to connect the joint 30 and the auxiliary frames 12, 22, in which case drawings for manufacture can be obtained especially easily from the CAD models of the components 31, 32. According to one embodiment of the invention, the adapter components 31, 32 are manufactured using a 3D printer, or by some other instant manufacturing method, by means of which it is possible to manufacture, for example, polymer parts directly with the aid of CAD models. Alternatively, it is possible to use some other CAD-CAM system, by means of which a component of sufficient strength can be created, and which can be manufactured rapidly. For example, the component can be machined from aluminium in a machining centre, or manufactured instantly using some other technologies. The manufacture of pieces directly on the basis of CAD models is, as such, known.

Once the adapter components 31, 32 have been manufactured, they are fitted to the corresponding auxiliary frames 12, 22. The auxiliary joint 30 is fitted between the adapter components 31, 32, in which case an anatomically personalized and mobilizing external support is created outside the joint 40 between the first and second bone groups 10, 20. As stated, the auxiliary joint 30 is preferably adjustable, in such a way that the angle between it and the movement of the actual joint 40 can be adjusted. Immediately after the operation, the auxiliary joint 30 is adjusted, preferably in such a way that the movement between the first and second bone groups 10, 20 does not permit the bone groups to fix. During the period of post-operative rehabilitation, the path and angle of the movement permitted by the auxiliary joint 30 is adjusted on the basis of the CAD model of the path to be anatomically correct and the extent of the paths of motion can be adjusted as required as care progresses.

According to one embodiment, the method according to certain embodiments of the invention is used in connection with a joint operation, in which operation a soft mass suitable for the purpose is utilized, which is arranged to differentiate in different support tissues when the joint experiences manipulation on the standard path. In the embodiment, the joint is operated on using the technique described, in which the destroyed joint surfaces are removed and is replaced by a mass like that described, which can differentiate into different types of tissue. In the embodiment, an external support, which is particularly advantageous in connection with precisely the said mass, is arranged for the joint that has been operated on.

Figure 4:
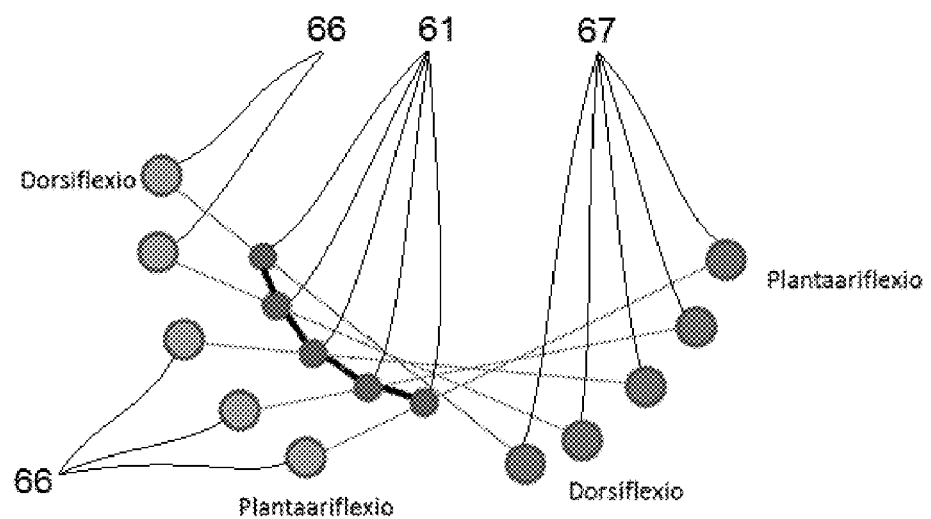
FIG. 4 illustrates a schematic sagittal view of an ankle movement along a path.
Figure 6:
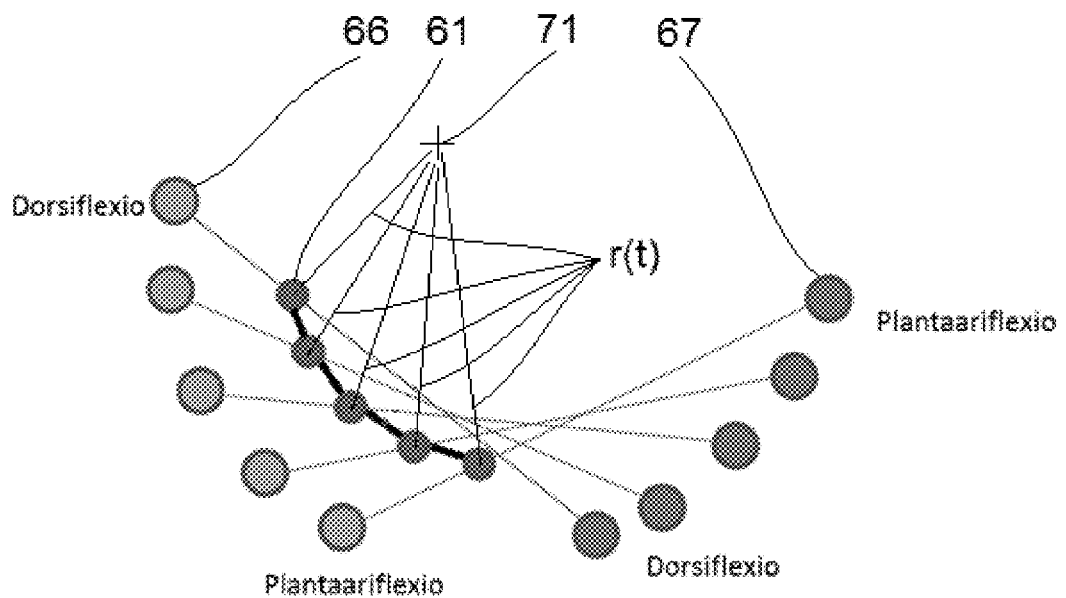
FIG. 6 illustrates a schematic view of the path of an axis of rotation relative to a stationary swing axis.

In FIG. 4 a schematic sagittal view of an ankle movement along a path is illustrated. One screw is invasively attached to the Talus and one screw is invasively attached to the Calcaneus. In the ankle example, the axis of rotation 61 of the Talus and Calcaneus typically describes a spline having a varying radius relative to a stationary swing axis 71. The stationary swing axis 71 is shown in FIG. 6. According to studies, the radius of this path may, for example, vary between r(t)=10 [mm] and r(t)=60 [mm]. The Talus screw 66 and the Calcaneus screw 67 are connected to the respective bone group and each of the aforementioned screws 66, 67 follows a spline or path during movement of the ankle complex. The axis of rotation 61 of the ankle complex is not stationary during movement of said ankle complex. The movement of said ankle complex is further anatomically personal.

In the following, certain embodiments of the external support according to the present invention are examined in greater detail in FIG. 5. Features of the external support described above can be also used in the embodiments of the external support described below. Also features of the method described above can be used in the embodiments of the method according to the invention.

Figure 5:
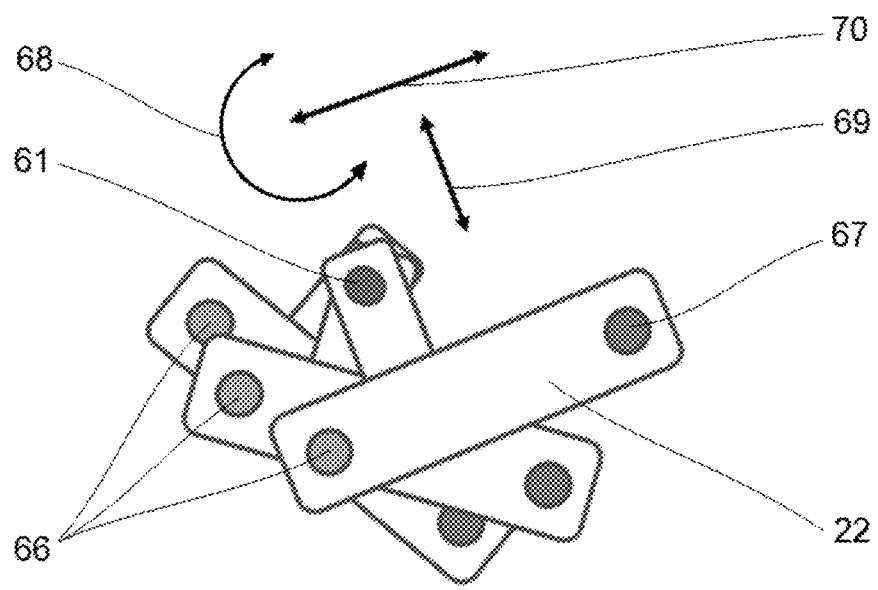
FIG. 5 illustrates a schematic view of an external auxiliary frame of an external support according to a certain embodiment of the invention.

In FIG. 5 a schematic view of an external auxiliary frame 22 of an external support according to a certain embodiment of the invention is illustrated. The anatomically personalized and mobilizing external support comprises at least one first external auxiliary frame 12, which is configured to be attached to a first bone group 10 using invasive attachment means. The first external auxiliary frame 12 is not shown in FIG. 5. The external support additionally comprises a second external auxiliary frame 22, which is configured to be attached to the second bone group 20. The second bone group 20 may be, for example, formed by the Talus and the Calcaneus. An external auxiliary joint 30 is fitted between the first and the second auxiliary frame 12, 22. According to certain embodiments, the at least one external auxiliary joint 30 is adjustable in such a way that the angle between the at least one external auxiliary joint 30 and the movement of a patient's joint between the first and second bone group 10, 20 can be adjusted.

Typically, the external support comprises bone screws or cables or both as invasive attachment means for fixing the at least one first external auxiliary frame 12 and the at least one second external auxiliary frame 22 to the first and second bone group 10, 20, respectively. In FIG. 5 the second external auxiliary frame 22 is configured to be invasively attached by means of a Talus screw 66 and a Calcaneus screw 67 to the Talus and to the Calcaneus, respectively. The first external auxiliary frame 12 is then configured to be invasively attached to the Tibia by means of, for example, two screws.

The external support is configured to permit a rotation 68 of the second external auxiliary frame 22 about a rotational axis 61 or centre point relative to the first external auxiliary frame 12. The radius r(t) between the rotational axis 61 or centre point and a stationary swing axis 71 can be varied by sliding of the rotational axis 61 or centre point relative to the first external auxiliary frame in a first direction 69. The stationary swing axis 71 is shown in FIG. 6. The radius r(t) between the rotational axis 61 or centre point and the stationary swing axis 71 can be further varied by sliding of the rotational axis 61 or centre point relative to the first external auxiliary frame in a second direction 70, which differs from the first direction 69. According to certain embodiments, it is also possible to slide at least a portion of the second external auxiliary frame 22 in the second direction 70, instead of offsetting the second external auxiliary frame 22 as such in the second direction 70. The stationary swing axis 71 is an imaginary axis which is typically arranged parallel to the rotational axis 61. The first sliding direction 69 can be, for example, arranged perpendicular to the second sliding direction 70. According to other embodiments, the first sliding direction 69 is not arranged perpendicular to the second sliding direction 70. According to certain embodiments, the first and second sliding directions 69, 70 are arranged perpendicular to the rotational axis 61.

In other words, by offsetting of the rotational axis 61 or centre point in a two-dimensional plane 63, a varying radius r(t) between the temporary position of the rotational axis 61 or centre point and the stationary swing axis 71 can be obtained, which varying radius r(t) essentially coincides or coincides with the natural movement of the ankle complex. The first sliding direction 69 may be, for example, arranged perpendicular to the second sliding direction 70. According to certain embodiments, the varying radius r(t) of the path of the rotational axis 61 or centre relative to the stationary swing axis 71, i.e. the varying distance between the temporary position of the rotational axis 61 or centre point and the stationary swing axis 71, may be, for example in the range between 10 [mm] and 60 [mm].

The external support according to certain embodiments of the invention can be therefore considered as external support comprising a multi-axis fixator apparatus.

According to certain embodiments, the anatomically personalized and mobilizing external support further comprises at least one personalized adapter component 31, 32, which is arranged to connect the auxiliary joint 30 to the first auxiliary frame 12 and which at least one external auxiliary joint 30 is made by additive manufacturing or machining. The at least one adapter component 31, 32 is not shown in FIG. 5.

According to certain embodiments, in the auxiliary frames 12, 22 there are measurement points, which are arranged to receive a measuring head of a coordinate measuring device. The measurement points and a coordinate measuring device are not shown in FIG. 5. According to other embodiments, it is possible to use, for example, a three-dimensional laser scanner or a camera based device for measurement.

In FIG. 6 a schematic view of the path of a rotational axis 61 relative to a stationary swing axis 71 is illustrated. The temporary radius r(t) between the stationary swing axis 71 and the rotational axis 61 or rotational centre point varies along the path of the ankle complex movement.

Current one-axis external fixator apparatuses having both bone screws and the stationary swing axis in one plane cannot provide a motion which coincides with the natural motion of the ankle complex. The current external fixator apparatuses can only provide a constant radius r between the stationary swing axis and the rotational axis or rotational centre point.

The external support according to certain embodiments of the present invention comprising a multi-axis fixator apparatus can vary the radius r(t) between the temporary position of the rotational axis 61 or centre point and the stationary swing axis 71, thus improving mobility. Mobilization improves healing results remarkably. A best fit rotation axis 61 can be personalized in the sagittal plane by these adjustment possibilities. Additionally, trauma recovery can be improved by means of the external support according to the embodiments of the invention.

Measurement methods described in this document as well as computer aided analysis/software can be, for example, used in order to enhance the result and the accuracy. The measurement is carried out after assembly of bone screws. The measurement provides e.g. movement data of an ankle from which data the optimal location of the rotation axis 61 and the personalized radius r(t) of the rotation axis 61 relative to the stationary swing axis 71 can be estimated. The multi-axis fixator is then adjusted correspondingly.

Figure 7:
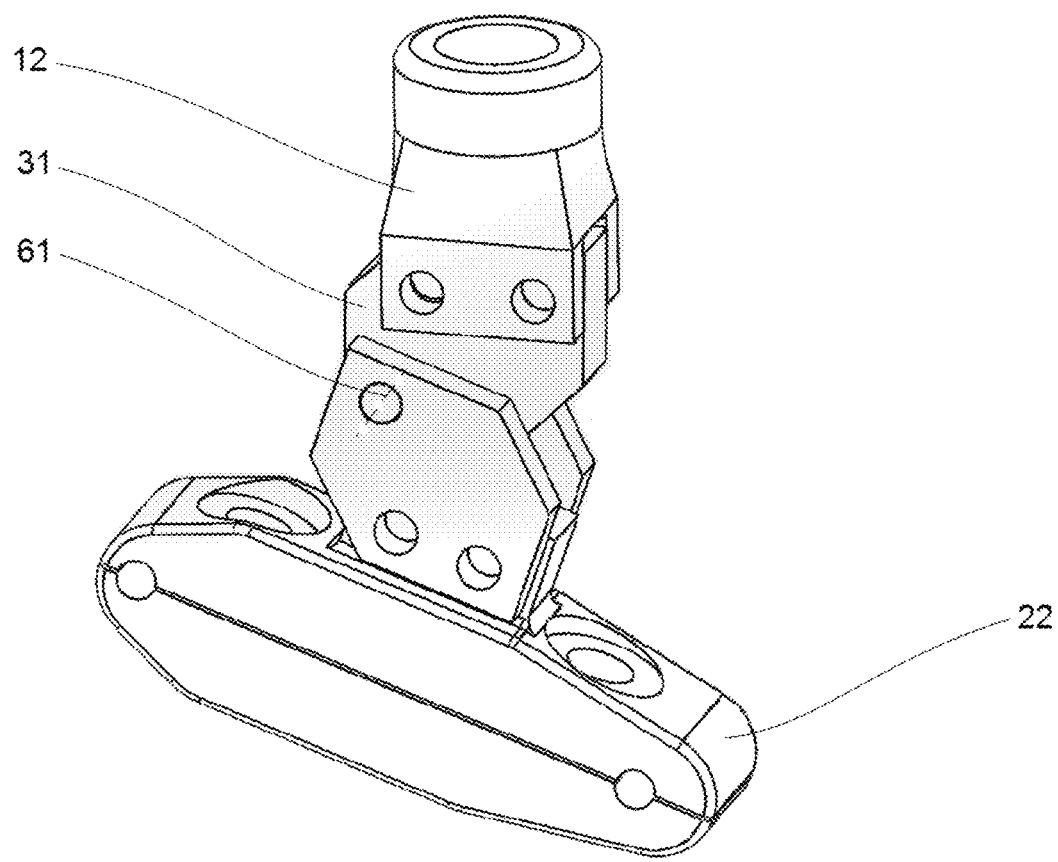
FIG. 7 illustrates a schematic view of an external auxiliary frame of an external support according to a certain embodiment of the invention.

In FIG. 7 a schematic view of an external auxiliary frame of an external support according to a certain embodiment of the invention is illustrated. The anatomically personalized and mobilizing external support is configured to be arranged to support a physical joint 40 between a first and a second bone group 10, 20. The external support comprises a first external auxiliary frame 12, which is configured to be attached to the first bone group 10 using invasive attachment means 21 and a second external auxiliary frame 22, which is configured to be attached to the second bone group 20 using invasive attachment means 21. The first external auxiliary frame 12 may comprise so called Ilizahrov rings which are not shown in FIG. 7. The invasive attachment means 21 may include, for example, bone screws which are also not shown in FIG. 7. The bone screws of the first external auxiliary frame 12 may be, for example, attached to the Tibia. The bone screws of the second external auxiliary frame 22 may be, for example, attached to the Talus and the Calcaneus. A personalized adapter component 31 is attached to the first external auxiliary frame 12. The personalized adapter component 31 is designed and manufactured according to measurement data. Suitable dimensions of the personalized adapter component 31 can be chosen after carrying out a measurement procedure described above. Other parts of the external support may be pre-designed. At least one external auxiliary joint 30 is fitted between the personalized adapter component 31 and the second auxiliary frame 22. Therefore, the external support is configured to permit a rotation of the second external auxiliary frame 22 relative to the first external auxiliary frame 12 about a rotational axis 61.

The embodiment described above, in which there is an anatomically personalized external support, designed, manufactured, and installed according to the invention, for repairing an ankle injury, is only one manifestation of the invention. The method according to the invention can also be applied to the rehabilitation of other joints, for instance the knee, elbow joint, or, for example, the wrist. Thus, the embodiment depicted above is not intended as a limiting specification, but rather as an exemplary description. One skilled in the art will naturally adapt the method, device, and use according to the invention to other than human patients. The present invention can also be implemented in a sequence differing from that described here. For example, the joint can be operated on and supported in the operation rigidly in a suitable manner, e.g., using a Ilizahrov ring. Once the joint permits movement, the rigid support can be removed and the invasive structures, i.e. auxiliary frames, can be utilized in measuring the movement of the joint, after which the necessary auxiliary joints and adapter components can be arranged according to the invention.

Although the present invention has been described in detail for the purpose of illustration, various changes and modifications can be made within the scope of the claims. In addition, it is to be understood that the present disclosure contemplates that, to the extent possible, one or more features of any embodiment may be combined with one or more features of any other embodiment.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

TABLE 1

List of reference numbers.

| Number | Part |
|---|---|
| 10 | first bone group |
| 12 | first auxiliary frame |
| 20 | second bone group |
| 21 | attachment means |
| 22 | second auxiliary frame |
| 30 | auxiliary joint |
| 31 | first adapter component |
| 32 | second adapter component |
| 40 | joint |
| 50 | seating |
| 51 | recess |
| 60 | CAD model of joint's kinetic dynamics |
| 61 | axis of rotation |
| 62 | centre point of rotation |
| 63 | plane of motion |
| 64 | path (measured points) |
| 66 | Talus screw |
| 67 | Calcaneus screw |
| 68 | rotation |
| 69 | first direction |
| 70 | second direction |
| 71 | stationary swing axis |
| r(t) | radius of rotational axis relative to stationary swing axis |
| t | time |

The invention claimed is:

1. An anatomically personalized and mobilizing external support configured to be arranged to support a physical joint between a first and a second bone group, which support comprises:
   at least one first external auxiliary frame, which is configured to be attached to the first bone group using invasive attachment means,
   at least one second external auxiliary frame, which is configured to be attached to the second bone group using invasive attachment means,
   at least one external auxiliary hinge type pin joint, which is fitted between the first and the second auxiliary frame, and
   wherein the external support is configured to permit, in a two-dimensional plane:
      rotation of the second external auxiliary frame relative to the first external auxiliary frame about a rotational axis which is defined by use of digitilization of movement,
      sliding of the rotational axis relative to the first external auxiliary frame in a first direction, and
      sliding of the rotational axis or at least a portion of the second external auxiliary frame relative to the first external auxiliary frame in a second direction, which differs from the first direction, and
   wherein the external support is configured to provide an elliptical path of the rotational axis of the second external auxiliary frame relative to the first auxiliary frame.

2. The anatomically personalized and mobilizing external support according to claim 1, wherein the external support is further configured to permit alteration of the radius of the rotational axis relative to a stationary swing axis.

3. The anatomically personalized and mobilizing external support according to claim 1, wherein the external support is configured such that the radius of a path of the rotational axis relative to a stationary swing axis is in the range between 10 mm and 60 mm.

4. The anatomically personalized and mobilizing external support according to claim 1 further comprising at least one personalized adapter component, which is arranged to connect the auxiliary joint to the first auxiliary frame.

5. The anatomically personalized and mobilizing external support according to claim 1, wherein the first sliding direction is arranged perpendicular to the second sliding direction.

6. The anatomically personalized and mobilizing external support according to claim 1, wherein in the auxiliary frames there are measurement points, which are arranged to receive a measuring head of a coordinate measuring device.

7. The anatomically personalized and mobilizing external support according to claim 1, wherein the at least one external auxiliary joint is adjustable in such a way that an angle between the at least one external auxiliary joint and the movement of a patient's joint between the first and second bone group can be adjusted.

8. The anatomically personalized and mobilizing external support according to claim 1, wherein the external support comprises bone screws or cables or both as invasive attachment means configured to fix the at least one first external auxiliary frame and the at least one second external auxiliary frame to the first and second bone group, respectively.

9. The anatomically personalized and mobilizing external support according to claim 1, wherein a personalized adapter component, which is arranged to connect the auxiliary joint to the first auxiliary frame, is manufactured using an instant manufacturing method.

* * * * *